United States Patent [19]

Simons et al.

[11] 4,401,118

[45] Aug. 30, 1983

[54] SWIMMING APPARATUS

[76] Inventors: Elliot Simons, 51 Broad Reach, #M-53A; Robert Boulos, 51 Broad Reach, #T-64A, both of North Weymouth, Mass. 02191

[21] Appl. No.: 267,690

[22] Filed: May 28, 1981

[51] Int. Cl.$^3$ .............................................. A61M 16/00
[52] U.S. Cl. ................................................. 128/207.14
[58] Field of Search ...................... 128/201.11, 207.14, 128/207.15, 207.17

[56] References Cited

U.S. PATENT DOCUMENTS

| | | | |
|---|---|---|---|
| 1,835,757 | 12/1931 | Burchett | 128/207.17 |
| 2,491,647 | 12/1949 | Colavita | 128/207.14 |
| 3,920,009 | 11/1975 | Olsen | 128/207.14 |
| 4,332,245 | 6/1982 | Boone | 128/207.14 |

FOREIGN PATENT DOCUMENTS 189504  4/1957  Fed. Rep. of Germany ........................ 128/201.11

OTHER PUBLICATIONS

Hauwaert, Paul V. G., "Larkel 2," Jul. 30, 1975, (advertisement).

*Primary Examiner*—Kyle L. Howell
*Assistant Examiner*—Harry J. Macey
*Attorney, Agent, or Firm*—Wolf, Greenfield & Sacks

[57] ABSTRACT

A swimming apparatus that permits an individual with a laryngectomy to be able to swim. The apparatus comprises a mouthpiece, a throat sealing member and an air tube intercoupling the mouthpiece and sealing member. The sealing member is securely disposed to cover and seal about the throat stoma while having an opening to permit air passage to the throat. The mouthpiece is controlled by the swimmer as a valve to control airflow through the unobstructed air tube.

12 Claims, 13 Drawing Figures

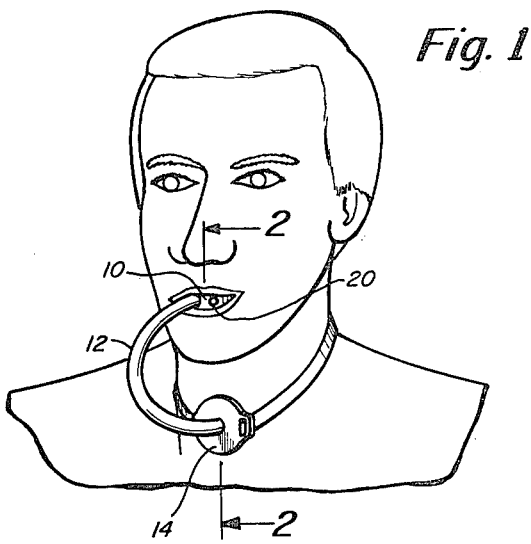
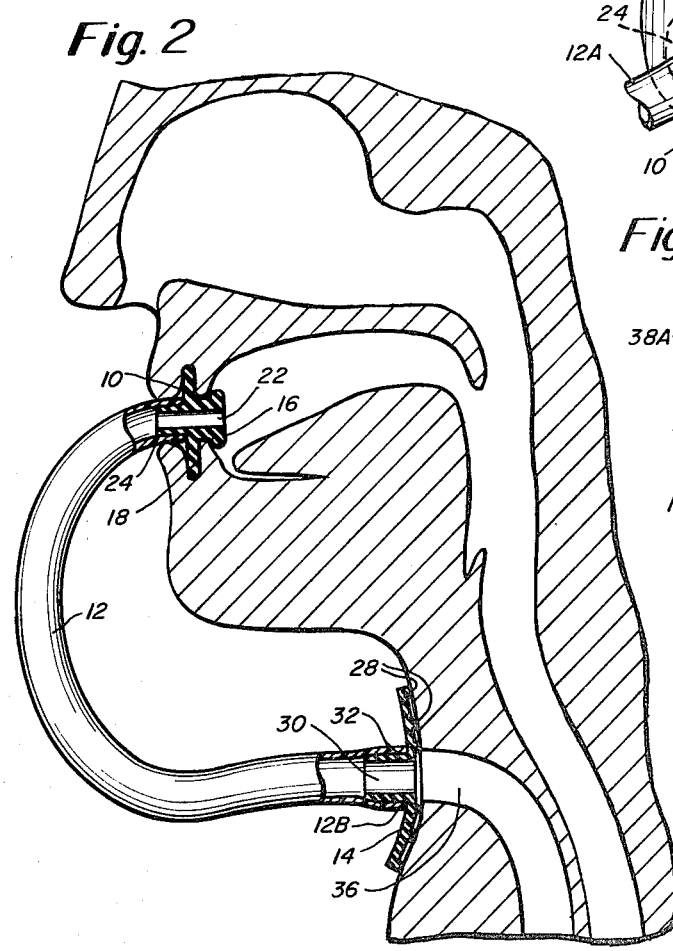
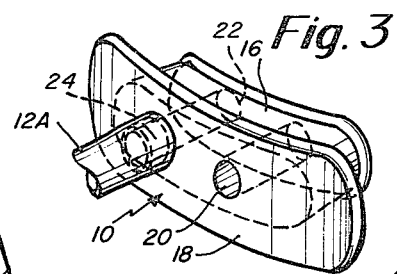
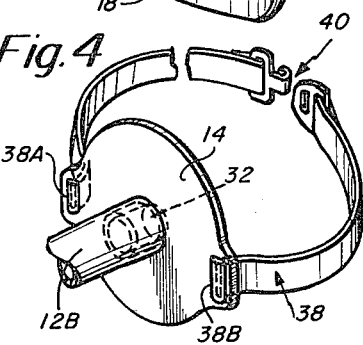
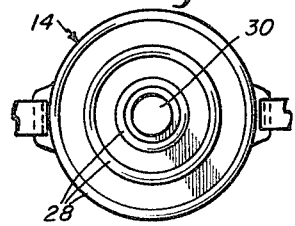

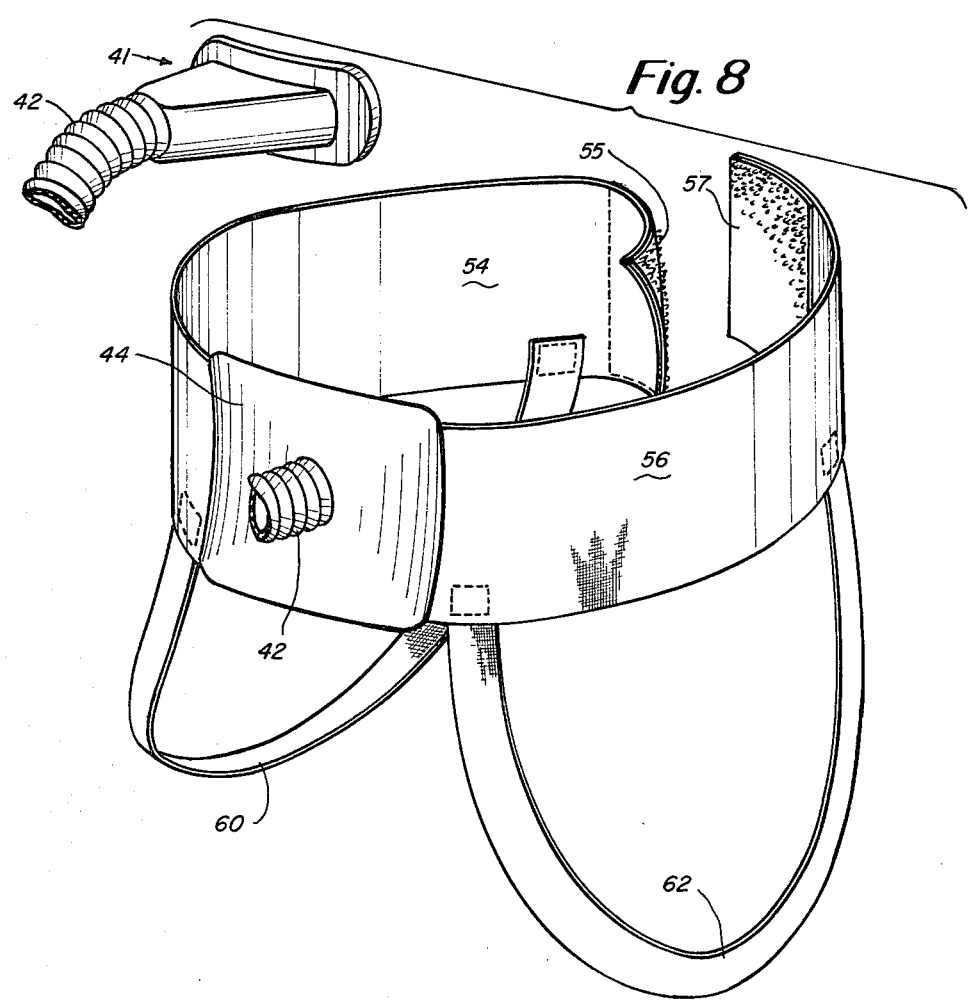

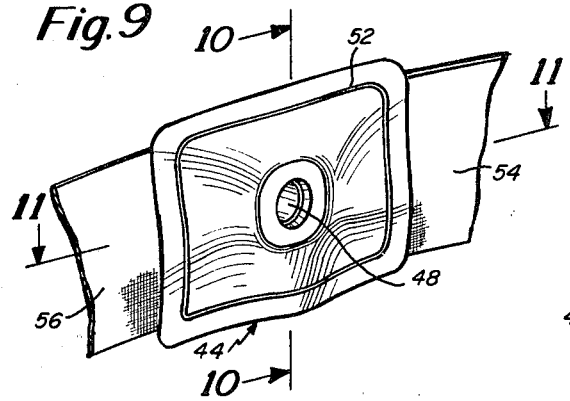
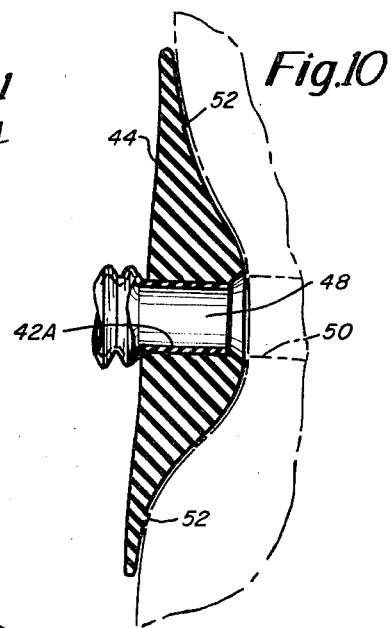
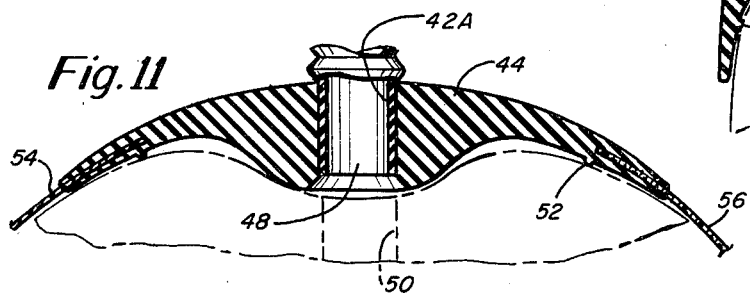
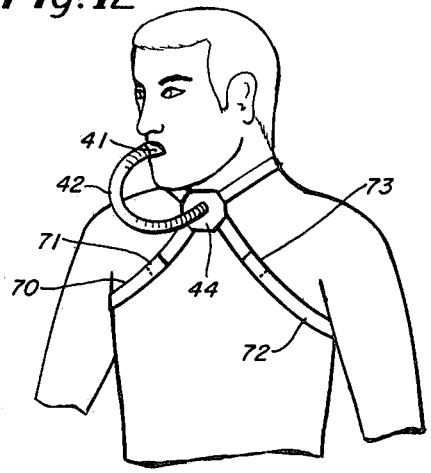
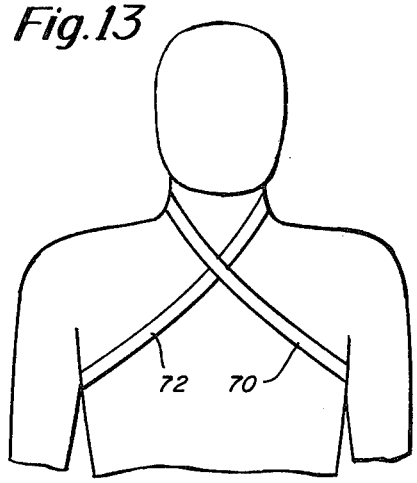

SWIMMING APPARATUS

BACKGROUND OF THE INVENTION

The present invention relates in general to a swimming apparatus, and more particularly to a swimming apparatus particularly adapted for use by an individual with a laryngectomy so as to enable that person to swim.

An individual that has had a laryngectomy is not able to enjoy swimming an other water activities because of the absence of control of air flow through the throat stoma. It is very unsafe to attempt swimming particularly where water can easily enter through the throat stoma.

Accordingly, it is an object of the present invention to provide an apparatus which will permit an individual with a laryngectomy to be able to swim safely.

Another object of the present invention is to provide a swimming apparatus in accordance with the preceding object and which is comfortable to wear, easy to attach to the swimmer, and adaptable for use by swimmers of virtually any age.

SUMMARY OF THE INVENTION

To accomplish the foregoing and other objects of this invention there is provided a swimming apparatus which is used to enable a person having a laryngectomy or the like to swim safely. This apparatus comprises an elongated unobstructed air tube, a mouthpiece means at one end of the air tube having an air passage communicating with the air tube to enable air passage between the air tube and the persons mouth and a relatively flat sealing member having means forming a water tight seal about the throat stoma. The sealing member also has an air passage and means are provided securing the other end of the air tube to the sealing member enabling air passage between the air tube and the persons throat. A means is provided for holding the sealing member in good sealing relationship to the throat about the throat stoma whereby the person can control air flow in alternate directions corresponding to inhalation and exhalation through the air tube by interaction of the mouth and mouthpiece. This interaction of the mouth and mouthpiece essentially forms a valve for controlling air flow via the air tube during both inhalation and exhalation. In one embodiment described herein the mouthpiece includes a vent adapted to be blocked and unblocked by interaction of the mouth with the vent to control air flow and also selectably block air flow to enable the swimmer to hold his or her breath. The air tube is described as either having a circular cross section and being in the form of a plastic tube or could be a more flexible tube such as one having a pleated configuration. Also, it is preferred that the sealing member be contoured to fit to the persons throat. A throat mold could be made so that the sealing member is personally fitted to the person that will be using it. The means for forming a water tight seal about the throat stoma may comprise a sealing ridge which is disposed about the periphery of the throat stoma. The means for holding the sealing member preferably includes a strap arrangement including in one embodiment a neck strap and associated fastener and in another embodiment both neck and arm straps. The arm straps have been found to be of advantage in that with the neck strap alone the sealing member may tend to ride up and thus the sealing member is more positively positioned by means of both a neck strap and arm strap.

BRIEF DESCRIPTION OF THE DRAWINGS

Numerous other objects, features and advantages of the invention should now become apparent upon the reading of the following detailed description taken in conjunction with the accompanying drawings in which:

FIG. 1 shows a first embodiment of the present invention as positioned on a user;

FIG. 2 is a cross-sectional view taken along line 2—2 of FIG. 1 showing the air passage communication between throat and mouth;

FIG. 3 is a fragmentary view showing the mouthpiece;

FIG. 4 is a fragmentary view showing the sealing member and associated strap;

FIG. 5 is a rear view of the sealing member showing the means for facilitating sealing to the throat about the throat stoma;

FIG. 6 is a front view of an alternate embodiment of the invention;

FIG. 7 is a rear view of the embodiment of FIG. 6 showing the rear strap arrangement;

FIG. 8 is a perspective view showing the mouthpiece and the sealing member and associated straps;

FIG. 9 shows a further detail on the inside of the sealing member;

FIG. 10 is a cross-sectional view taken along line 10—10 of FIG. 9;

FIG. 11 is a cross-sectional view taken along line 11—11 of FIG. 9;

FIG. 12 is a front view of still another embodiment of the invention employing a different strap configuration; and FIG. 13 is a rear view of the strap arrangement of FIG. 12.

DETAILED DESCRIPTION

The swimming apparatus of the present invention enables a person having had a laryngectomy to be able to swim. A first embodiment of the invention is shown in FIGS. 1-5, a second embodiment in FIGS. 6-11 and an alternate strap arrangement in FIGS. 12 and 13.

The first embodiment in FIGS. 1-5 shows the swimming apparatus in operative position on the person. This apparatus comprises a mouthpiece 10, an elongated unobstructed air tube 12, and a flat sealing member 14. The mouthpiece 10 has an innerside 16 and an outer flange plate 18. The plate 18 is adapted to fit between the mouth and the teeth in the normal manner of a mouthpiece. Extending through the mouthpiece is a passage 20 forming a vent which can be covered and uncovered by the tongue to control air flow therethrough into and out of the mouth. Adjacent to the passage 20 is another passage 22 having at its outer end a circular flange 24 adapted to receive the end 12A of the air tube 12, as clearly depicted in FIG. 3.

As indicated in FIG. 5, the sealing member 14 has a series of circular sealing ridges 28. There is also provided a hole 30 at the center of the sealing member 14 and having on the outer side thereof a circular flange 32 adapted to receive the other end 12B of the unobstructed air tube 12, as depicted in FIG. 4. The ends 12A and 12B of the tube 12 may be secured to the respective mouthpiece and sealing member by an adhesive material or some type of a clamp could be used. Also, vaseline may be used on the throat facing surface of the sealing member to provide a good seal against the throat with the passage 30, properly in line with the throat stoma 36.

The sealing member is held in tight relationship to the throat about the throat stoma by means of a strap 38 secured at ends 38A and 38B to the sealing member. The strap 38 also has a fastening means such as the means 40 shown in FIG. 4.

In the embodiment of FIGS. 1–5 during inhalation air passes through the vent 20 into the mouth where it is conveyed by the air tube to the throat stoma. In order to provide proper air passage and to prevent water from entering the throat stoma the strap holds the sealing member tight against the throat and the sealing ridges assist in providing a water tight seal. The breath may be held by sealing the vent 20 to hold the air in the lungs. Exhalation occurs through the air tube into the mouth and out of the vent 20.

In accordance with the invention the mouthpiece may be replaced by a nose piece in which case the breathing is controlled through the nose rather than the mouth. However, the mouthpiece version is preferred.

A second embodiment of the invention is shown in FIGS. 6–11 including a preferred strap construction. The apparatus comprises a mouthpiece 41, and elongated unobstructed tube 42, and molded sealing member 44. In this embodiment the air tube 42 has a pleated construction to enhance flexibility. In this embodiment the sealing member 44 is constructed preferably of a silicone (RTV) rubber and is molded to the configuration of the person. In this way the sealing member will fit tightly against the throat in alignment with the throat stoma. FIGS. 10 and 11 show the end 42A which is a straight end section, embedded within a passage in the sealing member 44. This provides a passage 48 that is adapted to be in line with the throat stoma 50. This embodiment also has a sealing ridge 52 about its perimeter as depicted in FIG. 9. Vaseline or the like lubricant may also be employed between the sealing member 44 and the throat surface. Also, a resilient rubber-like material may be used as a seal secured to the inner surface of the sealing member and disposed between the sealing member and the throat. Again, the purpose of any lubricant or resilient material along with the ridge 52 is to provide a water tight seal about the throat stoma. By contouring the inner surface of the sealing member to match that of the person's throat this also assures a water tight seal. The sealing member is held in place by means of a main strap comprising strap pieces 54 and 56 each having respective Velcro ends 55 and 57 to form a fastening means for the upper strap. There are also provided secured from the upper strap, lower straps 60 and 62 adapted to be placed under the arms as clearly depicted in FIGS. 6 and 7.

The throat stoma is generally located at a low position on the neck and thus with the use of only an upper strap, the sealing member may tend to ride up the throat and not properly provide a water tight seal. However, with the use of the two lower straps 60 and 62 there is sufficient downward force on the upper strap to maintain the sealing member in proper alignment with the throat stoma.

FIGS. 12 and 13 show respective front and rear views of a person with the swimming apparatus of this invention in a slightly different embodiment. In this version the mouthpiece, air tube and sealing member may be identical to that shown in FIGS. 6 and 7. Thus, as indicated in FIG. 12, there is shown the mouthpiece 41 interconnected by the air tube 42 to the sealing member 44. In this embodiment there are provided a pair of criss-cross straps 70 and 72. Each of these straps connect at one end to the sealing member 44 and extend downwardly under the armpit and crossing to the other side of the body in the rear as shown in FIG. 13 to pass over the shoulder near the neck for fastening to an opposite side of the sealing member 44. Each of these straps may be provided with, for example, a Velcro fastener shown in FIG. 12 as fasteners 71 and 73 associated respectively with the straps 70 and 72.

With regard to the first embodiment described herein, it is noted that a vent 20 is used. In the latter two embodiments, no vent is provided but instead the mouth can be parted from the mouthpiece to enable air to enter and leave the mouth.

Having described a limited number of embodiments of this invention, it should now be apparent to those skilled in the art that numerous other embodiments are contemplated as falling within the scope of this invention. For example, the mouthpiece may be substituted in another embodiment by a nose piece. Also, the mouthpiece may be simply formed by the end of the air tube rather than the special construction of mouthpiece particularly described herein.

What is claimed is:

1. A swimming apparatus used to enable a person having a laryngectomy or the like to safely swim, said apparatus comprising; an elongated unobstructed air tube, a mouthpiece means at one end of the air tube having an air passage communicating with the air tube to enable air passage between the air tube and person's mouth, a relatively flat sealing member having means forming a water tight seal about the throat stoma, said tube and said sealing member being absent of any structure to intrude into the throat stoma, said sealing member also having an air passage, means securing the other end of the air tube to the sealing member enabling air passage between the air tube and person's throat, and means holding the sealing member in water tight sealing relationship to the throat about the throat stoma, said means holding the sealing member comprising fastening means for holding the sealing member in a water tight position about the throat stoma and including means supplying some downward force for holding the sealing member properly sealed, whereby the person controls air flow in alternate directions corresponding to inhalation and exhalation through the air tube by interaction of the mouth and mouthpiece.

2. A swimming apparatus as set forth in claim 1 wherein said air tube is a circular cross-section plastic tube.

3. A swimming apparatus as set forth in claim 1 wherein said air tube has a pleated configuration to enhance its flexibility.

4. A swimming apparatus as set forth in claim 1 wherein said sealing member is molded to the contour of the person's throat.

5. A swimming apparatus as set forth in claim 1 wherein said means forming a water tight seal about the throat stoma comprises a sealing ridge.

6. A swimming apparatus as set forth in claim 5 wherein said ridge is disposed about the periphery of the throat stoma.

7. A swimming apparatus as set forth in claim 1 wherein said means holding the sealing member includes strap means.

8. A swimming apparatus as set forth in claim 7 wherein said strap means includes a neck strap and associated fastener.

9. A swimming apparatus as set forth in claim 1 wherein the water tight seal is provided only between the sealing member and the outer surface of the throat about the throat stoma.

10. A swimming apparatus as set forth in claim 1 and further including a resilient, rubber-like material employed as a seal secured to the inner surface of the sealing member and disposed between the sealing member and the throat.

11. A swimming apparatus used to enable a person having a laryngectomy or the like to safely swim, said apparatus comprising; an elongated unobstructed air tube, a mouthpiece means at one end of the air tube having an air passage communicating with the air tube to enable air passage between the air tube and the person's mouth, said mouthpiece blocking substantially the whole mouth but including a vent adapted to be blocked and unblocked by interaction of the tongue with the vent to control air flow and also selectively block air flow as in holding the breath, a relatively flat sealing member having means forming a water tight seal about the throat stoma, said sealing member also having an air passage, means securing the other end of the air tube to the sealing member enabling air passage between the air tube and person's throat, and means holding the sealing member in sealing relationship to the throat about the throat stoma, whereby the person controls air flow in alternate directions corresponding to inhalation and exhalation through the air tube by interaction of the mouth and mouthpiece.

12. A swimming apparatus used to enable a person having a laryngectomy or the like to safely swim, said apparatus comprising; an elongated unobstructed air tube, a mouthpiece means at one end of the air tube having an air passage communicating with the air tube to enable air passage between the air tube and person's mouth, a relatively flat sealing member having means forming a water tight seal about the throat stoma, said sealing member also having an air passage, means securing the other end of the air tube to the sealing member enabling air passage between the air tube and person's throat, and means holding the sealing member in sealing relationship to the throat about the throat stoma, whereby the person controls air flow in alternate directions corresponding to inhalation and exhalation through the air tube by interaction of the mouth and mouthpiece, said means for holding the sealing member including strap means, said strap means including a neck strap and associated fastener, and a second strap under the arm and coupled to the sealing member.

* * * * *